United States Patent [19]
Aida et al.

[11] Patent Number: 5,295,957
[45] Date of Patent: Mar. 22, 1994

[54] BREAST PUMP HAVING A PRESSURE ADJUSTING MECHANISM

[75] Inventors: Shigeru Aida; Hiroyuki Uehara, both of Chiba, Japan

[73] Assignee: Pigeon Co., Ltd., Tokyo, Japan

[21] Appl. No.: 811,936

[22] Filed: Dec. 23, 1991

[51] Int. Cl.$^5$ ............................................. A61M 1/06
[52] U.S. Cl. ........................................ 604/74; 604/75
[58] Field of Search ....................... 604/73-76, 604/246, 248, 313-316

[56] References Cited

U.S. PATENT DOCUMENTS

| | | | |
|---|---|---|---|
| 4,583,970 | 4/1986 | Kirchner | 604/74 |
| 4,673,388 | 6/1987 | Schlewsog et al. | 604/74 |
| 4,759,747 | 7/1988 | Aida et al. | 604/74 |
| 4,781,698 | 11/1988 | Parren | 604/248 |
| 4,883,464 | 11/1989 | Morifuki | 604/74 |
| 4,886,494 | 12/1989 | Morifuji | 604/74 |
| 4,950,236 | 8/1990 | Wilson | 604/74 |
| 4,964,851 | 10/1990 | Larsson | 604/248 |

Primary Examiner—Ralph Lewis
Attorney, Agent, or Firm—Wenderoth, Lind & Ponack

[57] ABSTRACT

A breast pump for extracting milk from a human breast includes an extracting cup and has an engagement portion for engaging the breast. A container has a mouth portion connected to the extracting cup. A milk receiving bag is mounted to the mouth portion and suspended in the container. An air suction source is connected to the container in order to produce air suction inside the container. An air path connects the interior of the extracting cup and the inside of the container, wherein the air suction creates a negative air pressure condition to assist in the suction of milk. The milk flows by gravity through the extracting cup and into the milk receiving bag without contact with the air suction source or the inside of the container.

24 Claims, 10 Drawing Sheets

BREAST PUMP HAVING A PRESSURE ADJUSTING MECHANISM

BACKGROUND OF THE INVENTION

1. Field of the Invention

The present invention relates to a breast pump for extracting milk from a human breast and collecting the extracted milk in a milk receiving bag. Further, the present invention relates to a pressure adjusting mechanism for adjusting the pressure applied by the breast pump, as well as a milk receiving bag for freezing the extracted milk.

2. State of the Prior Art

One conventional breast pump is disclosed in Japanese publication 41,364/1984. The breast pump described in this document has a section for producing suction on the breast that is electrically driven, a milk extracting section and a bottle. The suction section has a pressure adjusting knob and a pressure release button for changing the internal pressure by the introduction of outside air. The milk extracting section has a funnel-like receiver vertically connected to the bottle by the suction section.

When the electrically driven suction section is operated and the funnel-receiver applied to a breast, a negative pressure or suction is created in the milk extracting section for extracting milk. The extracted milk is guided to flow into the bottle.

However, the above-described conventional breast pump has the following disadvantages. The milk extracting section of the breast pump is connected to the bottle, and thus the extracted milk is collected in the bottle. Thus when milk is preserved in a home freezer, it has to be moved from the bottle to a suitable freezing bag. When the frozen milk is then used to feed a baby, it has to be moved back to the bottle, which involves removing the freezing bag from the freezer, defrosting the freezing bag and warming the bag up to a desired temperature. Thus the milk has to be moved at least two times when milk is frozen and subsequently defrosted to feed a baby. This not only involves some trouble in moving the milk back and forth, but because the milk is moved at least two times, there is a risk that the bottle and bag might become unsanitary.

SUMMARY OF THE INVENTION

The object of the present invention is to solve the above-described problems of the conventional breast pump. More specifically, the object of the present invention is to eliminate the necessity of moving milk back and forth between different containers between collection, freezing storage and use. More specifically, the object of the present invention is to collect extracted milk directly in a milk receiving bag that is suitable for freezing, defrosting and use in feeding a baby.

The above objects of the present invention are accomplished by a provision of a breast pump which has an extracting cup having an engagement portion for engagement with the breast. A container is connected to the extracting cup, the container having a mouth portion. A milk receiving bag is provided for mounting on the mouth portion of the container, thus being suspended in the container. An air suction source is connected to the container for producing an air suction condition inside the container. An air path connects the interior of the extracting cup and the inside of the container for application of the suction pressure to the breast at the extracting cup.

Preferably, an air suction release mechanism is provided on the extracting cup for releasing the suction on a breast. The release mechanism preferably takes the form of a valve in engagement with an aperture in the wall of the extracting cup. In a first embodiment according to the present invention the valve is connected to a valve stem extending through the aperture, the valve stem having a head that is biased by a spring to a closed position. The spring may be an elastic bellows having an air hole therein. In a second embodiment according to the present invention, a valve is biased against a valve seat by a spring provided in an aperture extending through the wall of the extracting cup, a suction release lever being provided for moving the valve off of the valve seat.

In a further preferred feature according to the present invention, the breast pump is provided with a pressure adjusting mechanism for adjusting the suction pressure on a breast in the extracting cup. Preferably the pressure adjusting mechanism is connected to a suction conduit connected to the container, the air suction source also being connected to the suction conduit. The air suction source, it is noted, may be a motorized air pump.

More specifically, the pressure adjusting mechanism preferably includes a body portion which has an air path communicating with the suction conduit, an opening being provided in the air path. A nozzle portion has a plurality of different diameter nozzle holes therein which communicate with the air path, the nozzle portion being fixed in the opening. A rotating member is provided in the opening and has a portion for selectively allowing a single nozzle hole to communicate the air path with the exterior air. A knob rotatably mounted on the body portion is connected to the rotating member for rotation thereof.

Preferably the nozzle portion comprises a nozzle plate which has a plurality of nozzle holes therein and an air path plate on the nozzle plate having a plurality of protrusions defining air path holes corresponding to the nozzle holes of the nozzle plate. The body portion, further, preferably has a protrusion extending through the nozzle plate and into an air path hole of the air path plate to fix the nozzle plate and air path plate in the body. The air path may comprise a partially annular groove in communication with each of the nozzle holes and air path holes. The rotating member has a disc covering the air path holes, and the portion of the rotating member for selectively allowing a single nozzle hole to communicate the air path with the exterior air is a cut-out portion in the disc. Preferably, the body portion has a plurality of notches therein, with the rotating member having a resiliently mounted projection thereon for engagement with the notches upon rotation, thereby giving positive indications of the position of the knob for selection of an air path and nozzle hole.

Further, the extracting cup according to the present invention preferably has a milk extracting conduit which communicates with the engagement portion, and a connecting portion at an end of the conduit for connecting the extracting cup to the container. The container has an upper end with external threads thereon, the milk receiving bag has a flange that is supported on top of the upper end and the connecting portion of the extracting cup has internal threads engaging the external threads of the upper end of the container and holds the flange of the bag on the upper end. The air path extends between the upper end of the container and the bag and the flange of the bag, and between the flange and the connecting portion of the extracting cup, thereby providing communication between the air suction source and the extracting cup. The air path is made up of grooves provided in the flange of the bag.

Preferably, the milk receiving bag comprises a bag body which has a sealed end and an open end. A mouth piece is mounted in the open end and sealed thereto, with a mouth piece having a cylindrical portion and a sealed plate sealing the mouth piece and the bag body. A lid is also provided for the milk receiving bag. Preferably, the sealed plate has an annular groove and a pull ring for unsealing the bag body upon use thereof.

According to the first embodiment of the present invention, the air suction source is a manual pump that is connected to a bottom cap of the container. According to the second embodiment of the present invention, the pump is motorized and mounted on the container. The motorized pump includes an electric motor, a diaphragm pump connected to the electric motor and a power supply for powering the electric motor. The container, further, has a bottom cap with an air passage therethrough and a holder mounted to the bottom cap. The holder holds the diaphragm pump, the electric motor and the power supply on the bottom cap.

According to a further feature of the present invention, a milk receiving bag is provided which can reduce the necessary defrosting and heating time of the frozen milk upon use by reducing the size of a lump of ice formed at the entrance to the milk receiving bag.

The milk receiving bag has a generally rectangular aspect, with a bag being sealed at one end and having an opening at its other end. A cylindrical mouth member is sealed to the opening of the bag, with a cylindrical mouth member having an upper annular flange. A cap is provided for the bag, which cap is placed on the flange of the cylindrical mouth member. The cap has an intrusive portion which intrudes into the cylindrical mouth member and thereby reduces the amount of space available for milk to freeze in the cylindrical mouth member. Thus the size of the lump of ice which is formed at the cylindrical mouth member is reduced and melting of the ice is made easier upon the use of the frozen milk.

Preferably, the intrusive portion has an inner cylindrical portion that extends axially, with a lower wall portion at a lower end thereof. An annular projection on the outside of the inner cylindrical surface seals the bag with the inner surface of the mouth member. The cup further has an outer cylindrical portion that is concentric and integral with the inner cylindrical portion. The outer cylindrical portion also has an annular projection on an inner surface thereof for engagement with the flange.

By using a milk receiving bag as discussed above with the breast pump according to the present invention, the milk extracted may be fed directly to a baby by employing a standard nipple with the milk receiving bag. Otherwise, the milk receiving bag can be removed from the container, capped and subsequently frozen. When the milk is then later used for feeding a baby, the frozen milk is easily defrosted and warmed to a suitable temperature.

With the arrangement according to the present invention, the milk receiving bag, further, can be placed in and removed from the container of the breast pump without human contact with the inside of the milk receiving bag. Thus contamination of the milk with bacilli from a human hand can be prevented. Further, the milk receiving bag is suitable for long preservation by freezing. And as the extracted milk can flow directly from the extracting cup into the milk receiving bag without touching the container or the pump, it is unnecessary to wash the pump or the container. Sanitary conditions overall are thus ensured, and clean milk can always be provided.

BRIEF DESCRIPTION OF THE DRAWINGS

Further objects, features and advantages of the present invention will be apparent to those of skill in the art from the following detailed description taken in conjunction with the accompanying drawings, wherein.

DETAILED DESCRIPTION OF THE PREFERRED EMBODIMENTS

FIGS. 1-4 illustrate a breast pump according to a first embodiment of the present invention, employing a hand-powered air suction source. A milk extracting cup 1 has a funnel shaped breast engaging portion 3. A milk extracting conduit 2 extends from the base of the breast engaging portion 3 to a connecting portion 4. The breast engaging portion 3 projects obliquely from the upper part of the connecting portion 4.

Figure 1:
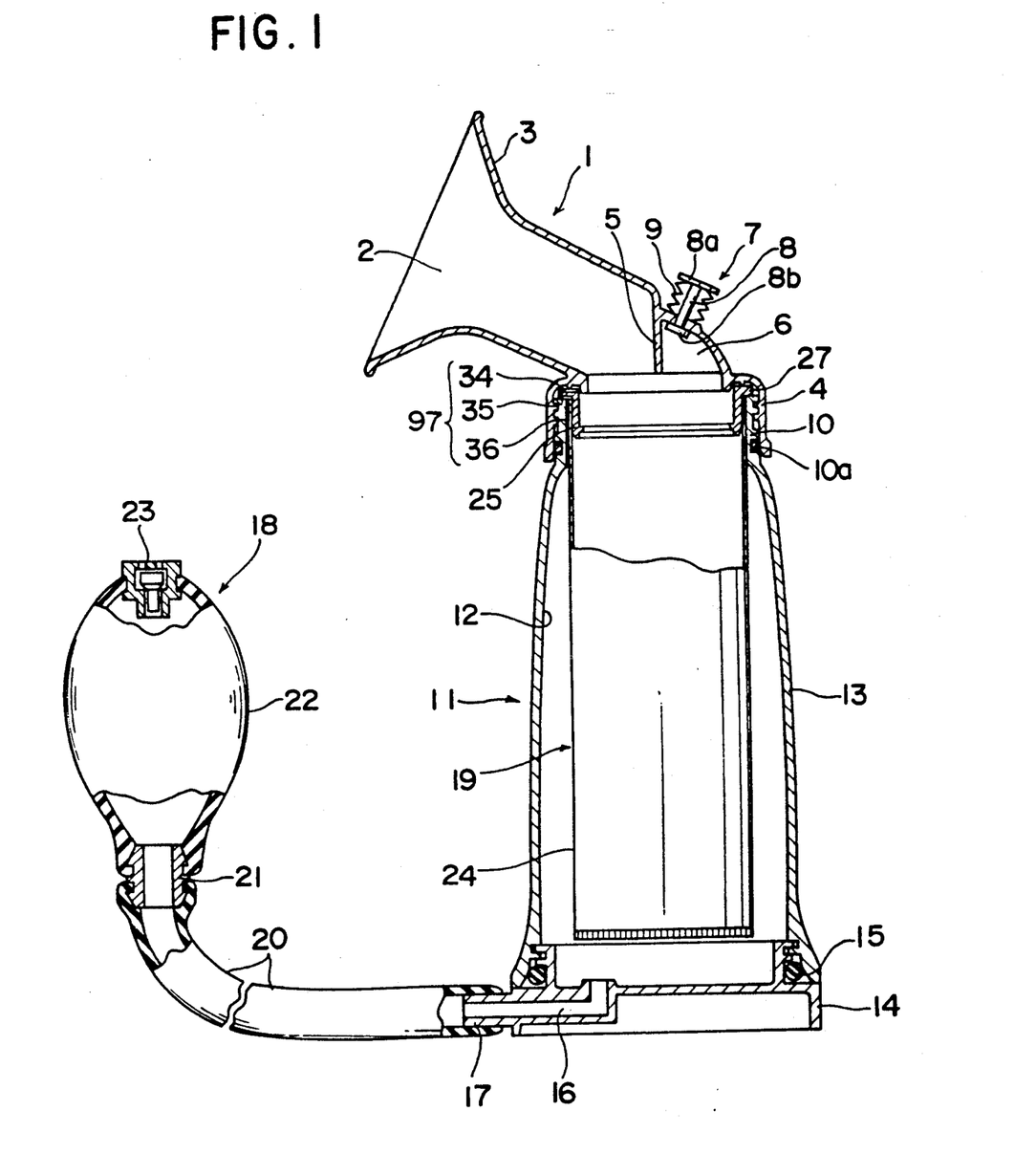
FIG. 1 is a partially cross-sectional view showing a first embodiment of the breast pump according to the present invention.
Figure 2:
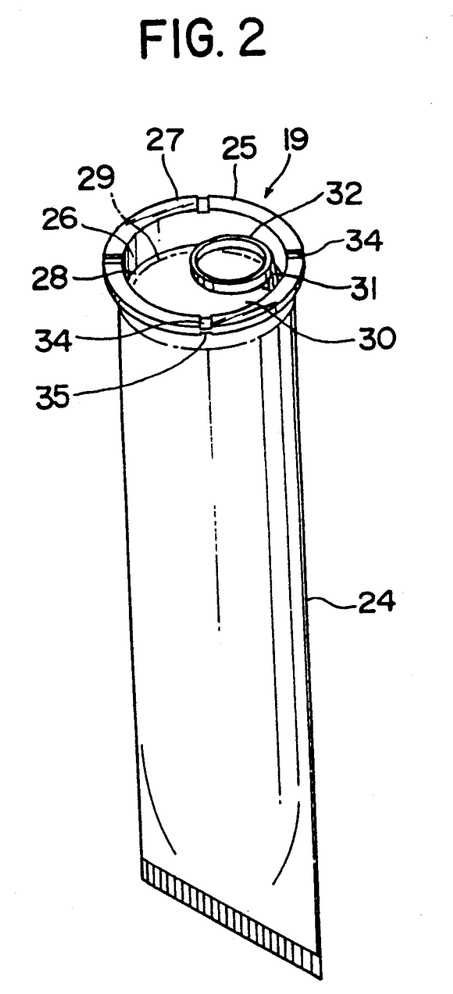
FIG. 2 is a perspective view of a milk receiving bag according to the first embodiment.

A chamber 6 is formed in the extracting cup 1 by a partition wall 5, separating the chamber 6 from the milk extracting conduit, at the upper part of the connecting portion 4. A pressure release mechanism 7 is connected to the chamber 6 for the release of the suction pressure or negative air pressure in the chamber 6 by allowing the admission of air.

The pressure release mechanism 7 includes a valve stem 8 having a head portion 8a and a valve 8b at opposite ends thereof. The valve stem extends through an aperture in the wall of the milk extracting cup 1. A spring arrangement 9 presses the valve stem outwardly by engaging the head portion 8a. The spring arrangement 9 may be a rubber elastic material having a bellows shape. An air hole (not shown) is preferably formed in the rubber elastic material for the admission of air. By the provision of the air hole, the head portion 8a may be pressed inwardly to release the suction inside the milk extracting cup 1. When the head portion 8a is released, the spring arrangement 9 presses the head portion 8a outwardly and the valve 8b closes the aperture, allowing air suction or negative air pressure to be generated in the milk extracting cup 1.

A female screw or thread is formed on the inner circumferential surface of the connecting portion 4. A container 11 has a substantially cylindrical body 13 with an upper end having a mouth 10. The mouth 10 has a male thread on the outer circumferential surface thereof threaded together with the female thread of the connecting portion 4. A bottom cap 14 is detachably connected to the bottom of the cylindrical body 13, and may be detached by unscrewing, for example. A seal member 15, such as an O-ring, is inserted between the cylindrical body 13 and the bottom cap 14 for the provision of an airtight connection.

An air passage 16 is formed through the bottom cap 14 to the interior of the container 11. The other end of the air passage 16 has a projecting portion 17 for connection to a hand-powered pump 18, used as an air suction or negative air pressure source.

The hand-powered pump 18 includes a rubber hose 20 that is connected to the projecting portion 17 and a rubber pump body 22 that is connected to the rubber hose 20 by a joint member 21. The pump body 22 also has an exhaust valve 23, as illustrated in FIG. 1.

A milk receiving bag 19 is suspended in the container 11. The milk receiving bag 19, as illustrated in FIGS. 1-4, has a rectangular bag body 24 having one end sealed and the other end with a mouth formed by member 25 tightly mounted to the inside of the open end of the bag body 24. The member 25 forming the mouth may, for example, be mounted to the bag body 24 by an adhesive or a heat melting method in which both the bag body 24 and the member 25 are made of a thermoplastic resin and fixed by heat.

Figure 3:
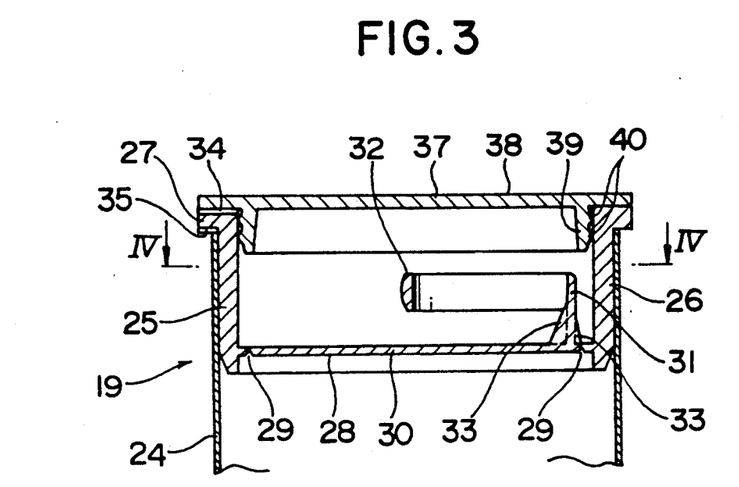
FIG. 3 is a cross-sectional view of a mouth portion of the milk receiving bag of FIG. 2.
Figure 4:
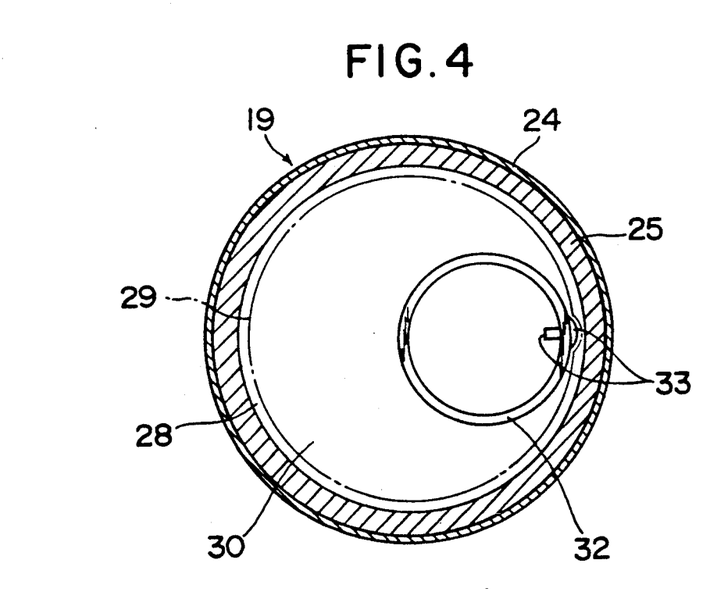
FIG. 4 is a cross-sectional view taken along lines IV—IV of FIG. 3.

Enlarged views of the member 25 are shown in FIGS. 3 and 4. The member 25 has a cylindrical portion 26 and a sealed plate 28 for sealing the inner end of the cylindrical portion 26. A fine annular groove 29 which is concentric with the cylindrical portion 26 is provided adjacent the outer periphery and on the underside of the sealed plate 28.

A central portion 30 of the sealed plate 28 may be easily pulled out due to the fine groove 29. A projection 31 is mounted on the outer portion of the central portion 30, and a pull ring 32 is mounted on top of the projection 31. A rib 33 reinforces the base of the projection 31.

A flange 27 is formed on the outer end of the cylindrical portion 26. A plurality of grooves 34 and 35 are formed on upper and lower parts of the flange 27, respectively. The grooves extend radially toward the center of the member 25.

Referring again to FIG. 1, note that the external diameter of the bag body 24, which is fixed to the cylindrical portion 26, is formed slightly smaller than the inner diameter of the mouth 10 of the container 11, thus obtaining a circumferential clearance 36 between the container 11 and the bag body 24. Thus when the milk receiving bag 19 is mounted in the space 12 of the container 11, and the milk extracting cup 1 is mounted to the container 11, the inside of the milk extracting cup 1 is connected to the inside of the container 11 via the radial grooves 34 and 35 and the circumferential clearance 36. The grooves 34 and 35, and the circumferential clearance 36, make up an air path 97, as illustrated in FIG. 1, communicating the extracting cup 1 with the air suction source 18.

Noting FIG. 3, a cap 37 can be provided to cover the member 25. The cap 37 has a surface 38 about the same size as the flange portion 27 of the member 25 and a cylindrical portion 39 extending down from the surface 38. The portion 39 can be inserted into the cylindrical portion 26 to provide an airtight closure of the open mouth of the member 25. At least one circular projecting portion 40 is provided about the cylindrical portion 39 to provide the airtight seal of the cylindrical portion 26.

The bag body 24, the member 25 and the cap 37 are all made from a material that is chosen so as to be harmless to the human body and which has good chemical stability, due to their function in receiving and restoring reserved milk from the human body. The materials should also be suitable for preservation by a freezer, for example to approximately 20° C. below zero. A tubular film made of nylon and polyethylene laminated together may be used for the material of the bag body 24. The member 25 and the cap 37 are suitably made of polyethylene resin.

Also provided is a seal 10a, as illustrated in FIG. 1, made of a suitable material for maintaining an airtight condition in the container 11 by sealing between the connecting portion 4 of the extracting cup 1 and the mouth 10 of the container 11.

The operation of the above embodiment of the present invention preferably proceeds as follows. When extracting milk with the above-described apparatus, one hand holds the connecting portion 4 of the extracting cup 1, and the breast engaging portion 3 is pressed to the breast. At the same time, the hand powered pump 18 is operated by the other hand of the user.

The air in the extracting cup 1 and the milk receiving bag 19 flows into the container 11 via the grooves 34 and 35 in the flange 27 of the member 25 and the circumferential clearance 36, i.e. the air path 97. The air in the container 11 flows from the air passage 16 to the atmosphere through the rubber hose 20, the rubber pump body 22 and the exhaust valve 23. By this airflow, a suction or negative air pressure condition is created inside the extracting cup 1 and the container 11, and suction is applied to the breast. By this suction, milk is extracted from the breast.

The extracted milk flows into the milk receiving bag 19 through the conduit 2 of the breast engaging portion 3 and the connecting portion 4 by gravity, and is then held in the receiving bag 19.

If pain or discomfort to the breast is caused by increasing the suction to too great an extent, or the milk extracting process is finished, the pressure release button 7 on the extracting cup 1 can be pushed for releasing the suction in the extracting cup 1. By releasing the suction and reducing the suction pressure on the breast, the extracting cup 1 can be removed therefrom.

One advantage of the present invention is that the milk extracted by the above method can be fed directly to the baby merely by exchanging the extracting cup 1 for a nipple.

When the extracted milk is not fed to the baby immediately, the milk receiving bag 19 can be removed from the container and the cap 37 mounted on the member 25 to seal the bag. The sealed milk receiving bag can then be preserved in a frozen form in a home freezer.

When the frozen milk is to be used, the milk is defrosted and warmed to a suitable temperature. If the inside of the milk receiving bag 19 is sterilized in advance, the milk can be preserved in a sanitary condition. The milk receiving bag can also be inserted into and removed from the container 11 without the user's hand touching the inside of the milk receiving bag 19 or the container 11. Thus the invention according to the first embodiment is able to prevent the milk from being contaminated by bacilli which may be carried by the hand of the user. The milk in the milk receiving bag 19 is thus capable of being frozen for long periods of preservation.

Because the extracted milk flows directly into the milk receiving bag 19 from the extracting cup 1, without touching the container 11 and the hand powered pump 18, no milk flows in the inside portion of the pump 18. It is thus unnecessary to wash or clean the hand powered pump 18 and the container 11, these being troublesome to wash. The present invention can thus provide a breast pump in which clean, sanitary milk can always be obtained.

FIGS. 5-14 illustrate a second embodiment of the breast pump according to the present invention. The breast pump according to the second embodiment uses an electric motor to drive a suction pump for generating the negative air pressure.

Figure 5:
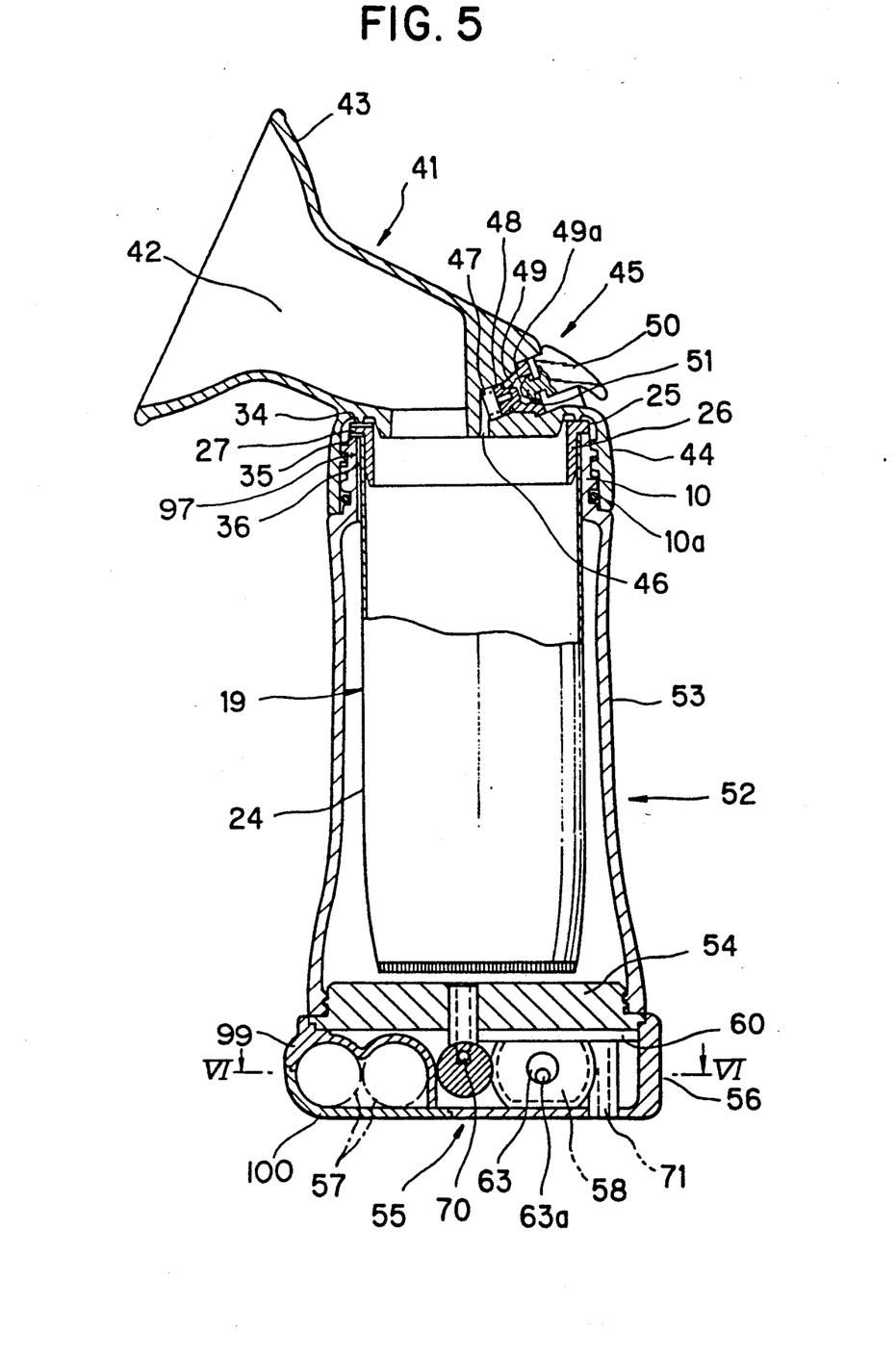
FIG. 5 is a partially cross-sectional view showing a second embodiment of a breast pump according to the present invention.

FIG. 5 illustrates an extracting cup 41. The extracting cup 41 has a breast engaging portion 43 with milk extracting conduit 42 and a connecting portion 44 extending from the base of the breast engaging portion 43. A pressure release lever 45, differing from the pressure release mechanism of the first embodiment, is mounted near the base of the extracting cup 41.

The pressure release lever 45 has a spring 47 that is inserted into an opening or release path 46 formed in the side of the extracting cup 41. A valve 48 is loosely inserted in the release path 46, and is pressed by the spring 47 outwardly. A valve receiving member 49 having a valve seat is pressed into the release path 46 to maintain the valve 48 in the release path 46. A lever body 50 is slidably supported on the extracting cup 41. The valve receiving member 49 has a hole 49a extending through its center. One side of the hole 49a forms the valve seat for the valve 48. The valve seat is conically shaped for engaging the valve 48 with a tapered surface. A projection 51 is formed on the lever body 50 and is slidably inserted into the hole 49a through the side thereof opposite to the valve 48. The projection 51 has a point for engaging the valve 48.

The force of the spring 47 against the valve 48 presses the valve against the valve seat of the valve receiving member 49 to close the hole 49a and maintain an airtight condition in a container 52. When the lever body 50 is pressed, the projection 51 moves forward and the valve 48 is pushed back against the force of the spring 47. A tapered portion of the valve 48 is then moved apart from the tapered surface of the valve seat of the valve receiving member 49. The inside of the extracting cup 41 is thus connected with the atmosphere through the hole 49a, around the outside of the valve 48 and through the release path 46.

The container 52 includes a substantially cylindrical body 53 having an open top and bottom, and a bottom cap 54 detachably mounted to the bottom of the cylindrical body 53. The bottom cap 54 is mounted to a casing 56 in which an electrical suction source 55 is installed.

The electrical suction source 55 includes a motor 58 that is driven by dry batteries 57, a diaphragm suction pump 59 driven by the motor 58, a holder 60 for fixing the motor 58, the batteries 57 and the pump 59 to the bottom cap 54, a pressure adjusting mechanism 61 mounted to the holder 60 and an operating switch 62. The motor 58 is mounted in the holder 60. A crank member 63 having an eccentric shaft 63a is fixed to the rotating shaft of the motor 58.

Figure 6:
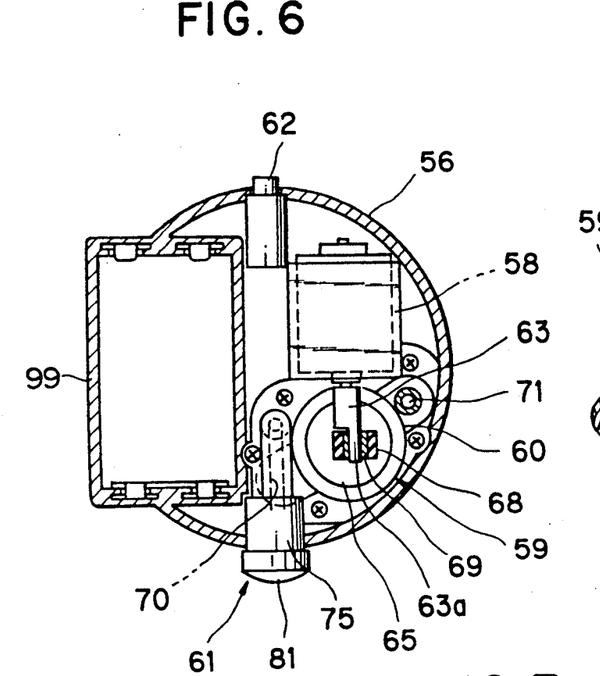
FIG. 6 is a cross-sectional view taken along lines VI—VI of FIG. 5.
Figure 7:
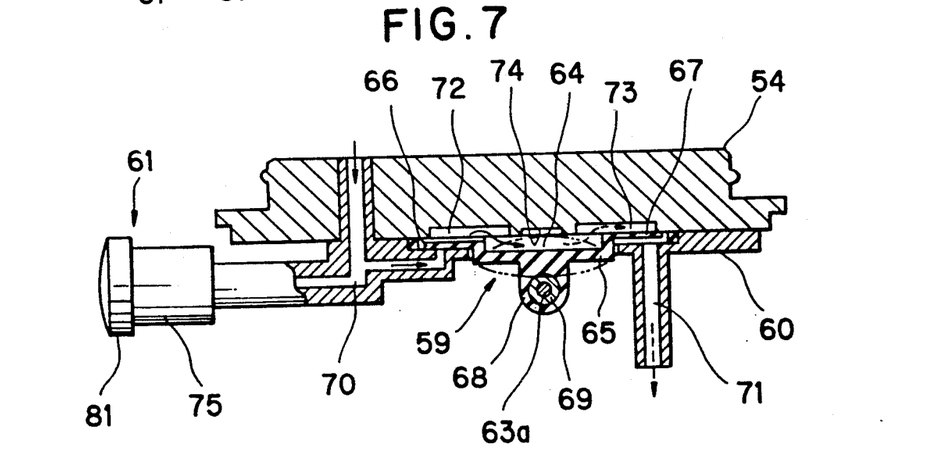
FIG. 7 is a cross sectional view of a main portion of an electrically driven air suction source of the breast pump of FIG. 5.
Figure 8:
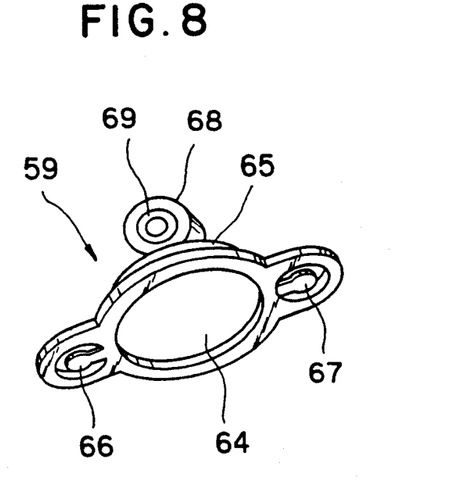
FIG. 8 is a perspective view of a diaphragm type suction pump.

The suction pump 59, as illustrated in FIGS. 6-8, includes a diaphragm 65 defining a pump chamber 64 having a central portion that expands circularly. A suction valve 66 and an exhaust valve 67 extend from a flange portion of the diaphragm 65. A boss 68 is formed on the expanding side of the diaphragm 65. A sleeve 69 is pressed into the boss 68 on the diaphragm 65, and the eccentric shaft 63a is rotatably inserted into the sleeve 69. The suction pump 59 is held on the bottom cap 54 by the holder 60, which covers the suction pump 59 except at the diaphragm 65.

The hollow for mounting the flange of the diagram 65, including the suction valve 66 and the exhaust valve 67, is formed on the holder 60. An air path 70 and an exhaust path 71 are also formed in the holder 60 as illustrated in FIG. 7. The air path 70 connects with the hollow of the holder 60 at the suction valve 66, and the exhaust path 71 connects with the hollow of the holder 60 at the exhaust valve 67. Further note that the air path 70 also connects with the inside of the container 52, extending through the bottom cap 54, and further connects with the pressure adjusting mechanism 61. The exhaust path 71 connects the exhaust valve 67 with the atmosphere, the exhaust path 71 extending through the casing 56.

A suction path 72 and an exhaust path 73 are formed on the bottom cap 54, as further illustrated in FIG. 7. The suction path 72 connects with the pump chamber 64 and the hollow of the holder 60 at the suction valve 66. The exhaust path 73 connects with the pump chamber 64 and the hollow of the holder 60 at the exhaust valve 67. On the center of the bottom cap 54 is formed a hollow 74 for preventing the diaphragm 65 from touching the bottom cap 54.

The pressure adjusting mechanism 61 is illustrated in FIGS. 9-14. A body 75 of the pressure adjusting mechanism 61 is integrally formed with the holder 60. The body 75 has an opening 76 at an end thereof which connects with the air path 70. See FIG. 9.

Figure 10A:
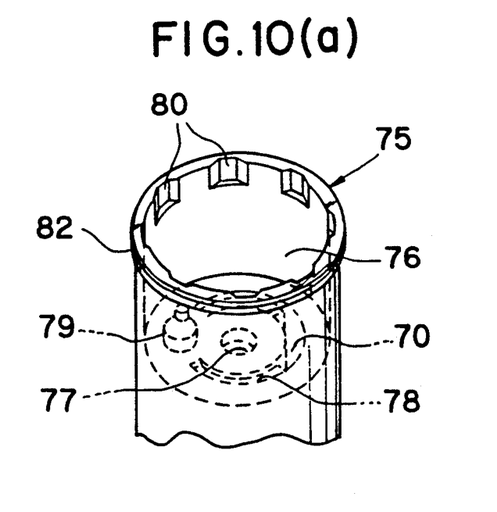
FIG. 10(a) is a perspective view of a body portion of the pressure adjusting mechanism of FIG. 9.
Figure 10B:
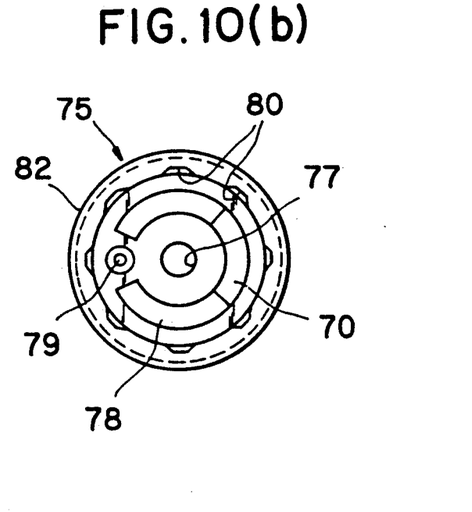
FIG. 10(b) is a plan view of the body portion of FIG. 10(a)

At the bottom surface of the opening 76, as illustrated in FIGS. 10(a) and (b), is a centrally located shaft receiving hole 77. A circular air path groove 78 extends around the shaft receiving hole 77 and connects with the air path 70. There is also provided a protrusion 79 between the ends of the air path groove 78.

On the inside of the upper end of the opening 76 are formed V-shaped notches 80 at equally spaced intervals. A flange 8 extends about the outer circumference of the opening 76, and prevents a knob 81 mounted on the end of the opening 76 from coming off of the body 75.

Figure 9:
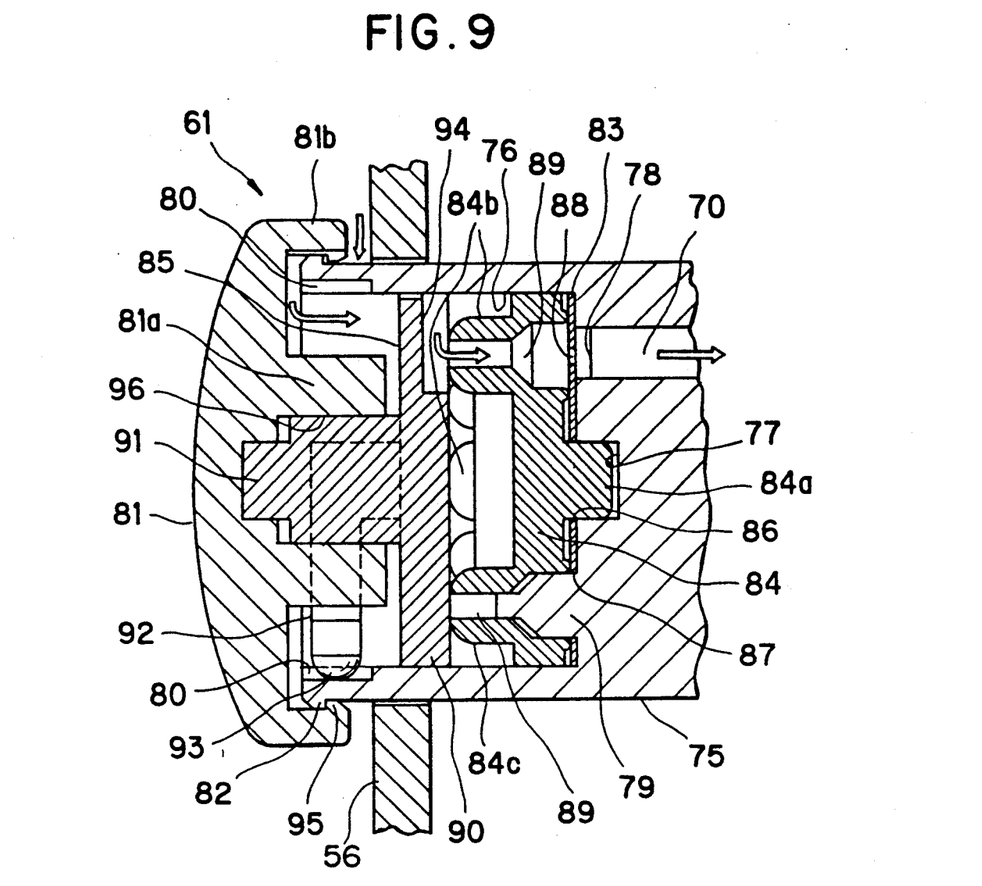
FIG. 9 is a cross-sectional view of a pressure adjusting mechanism.

A nozzle arrangement includes a nozzle portion having a nozzle plate 83 and an air path plate 84, as well as a rotating plate 85, all contained inside the opening 76.

Figure 11:
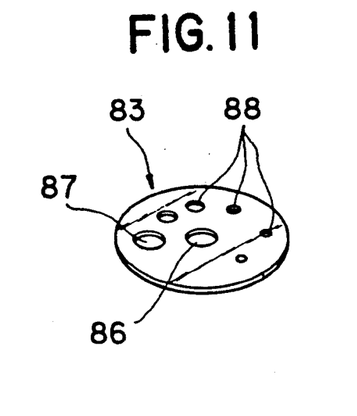
FIG. 11 is a perspective view of a nozzle plate.

The nozzle plate 83, as shown in FIG. 11, is a circular plate that has a central hole 86 that is the same size as the shaft receiving hole 77. A hole 87 is also provided for having the protrusion 79 extend therethrough and affix the nozzle plate 83 inside of the opening 76. Nozzle holes 88, each having a different diameter, are concentrically provided about the center hole 76 for connection with the circular air path groove 78.

Figure 12:
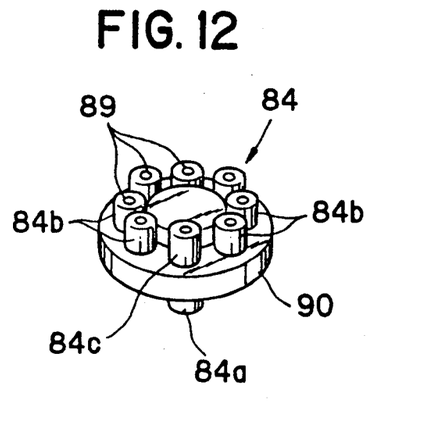
FIG. 12 is a perspective view of an air path plate.

The air path plate 84 is illustrated in FIG. 12. A shaft 84a is formed on one side thereof for insertion into the shaft receiving hole 77 through the center hole 86 of the nozzle plate 83. On the other side of the air path 84 are provide protrusions 84b corresponding to respective nozzle holes 88 of the nozzle plate 83. Each protrusion 84b has an air path hole 89 therethrough. The protrusion 89 is inserted into one of the air path holes 89 for preventing the rotation of the air path plate 84.

Figure 13A:
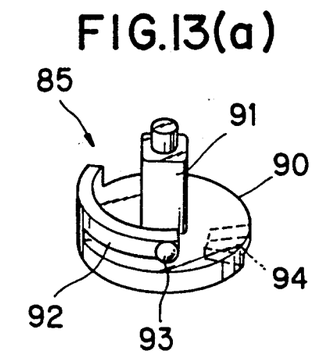
FIG. 13(a) is a perspective view of a rotating member.
Figure 13B:
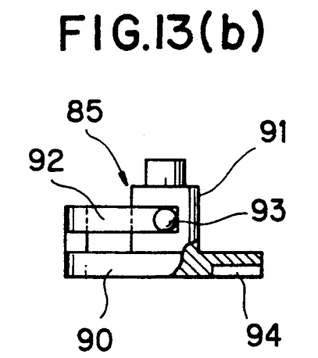
FIG. 13(b) is an elevational and partially sectional view of the rotating member of FIG. 13(a)

Each air path hole 89 may be shut by the rear face of the rotating plate 85. The rotating plate 85 is illustrated in FIGS. 13(a) and (b). The rotating plate 85 includes a disk 90 for loose insertion into the opening 76, an angular shaft 91 formed at the center of the disk 90 and an arc-shaped arm 92 extending about the periphery of the disk 90. The arc-shaped arm 92 has a projection 93 at the end thereof. On the bottom of the disk 90 is a fan-shaped cut out 94. The cut out 94 is used to connect with only a single one of the air path holes 89 of the air path plate 84 at a time.

Figure 14:
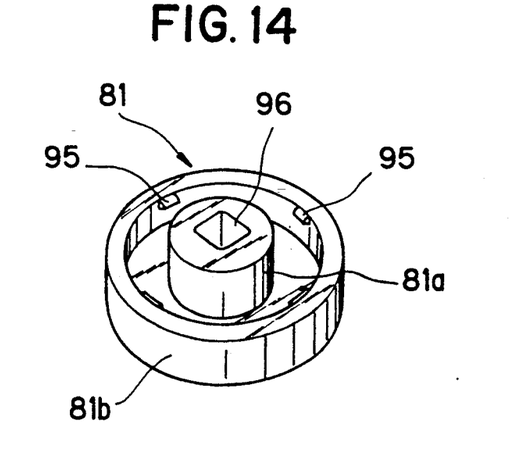
FIG. 14 is a perspective view of a knob.

The knob 81 is shown in FIG. 14, and has an inner cylindrical portion 81a and an outer cylindrical portion 81b. A plurality of nails 95 are formed on the inner side of the outer cylindrical portion 81b for engaging the flange 82 for preventing the knob 81 from coming off of the body 75. The inner cylindrical portion 81a has a centrally located angular hole 96 for receiving the angular shaft 81 of the rotating plate 85. Accordingly, the knob 81 can be used to rotate the rotating plate 85.

Noting again FIG. 5, a battery box 99 is formed with the casing 56. A battery cover 100 is detachably mounted on the battery box 99.

The operation of the above-described second embodiment according to the breast pump of the present invention is as follows. Essentially, the process of extracting milk by the use of suction or negative air pressure in the extracting cup 41 and the container 52 is similar to the first embodiment. Accordingly, only the movements of the suction pump 59, the pressure adjusting lever 45 and the pressure adjusting mechanism 41 which are different from the first embodiment will b described.

The suction pump 59 is started by the operation of the operating switch 62. When the motor 50 is turned on by the operating switch 62, the crank member 63 fixed to the rotating shaft of the motor 50 begins to rotate. By this rotation, the boss 68 and the diagram 65 reciprocate in a range of motion twice that of the eccentric range of the eccentric shaft 63a by the sleeve 69 in which the eccentric shaft 63a is inserted.

When the volumetric capacity in the pump chamber 64 is reduced by the movement of the diagram 65 toward the bottom cap 54, the air in the pump chamber 64 closes the suction valve 66 by the suction path 72 and opens the exhaust valve 67 by the exhaust path 73. The positive pressure in the pump chamber 64 presses the suction valve 66 closed to close off the air path 70 and opens the valve 67. Accordingly, the air in the pump chamber 64 is exhausted from the exhaust path 73 through the exhaust valve 67 and the exhaust path 71.

When the volumetric capacity in the pump chamber 64 is increased by the movement of the diagram 65 in a direction away from the bottom cap 54, the suction in the pump chamber 64 pulls the exhaust valve 67 toward the exhaust path 73 and separates the suction valve 66 from the air path 70. Thus the exhaust paths 71 and 73 are closed and the suction path 72 and air path 70 are opened. Therefore the air in the container 52 is sucked by the pump chamber 64 through the suction valve 66 from the air path 70.

By repeating this operation of the diagram suction pump 59, the container 52, the extracting cup 41 and the milk receiving bag 19 are exhausted of air, and a negative air pressure, or suction pressure, is generated. Thus milk can be extracted from a breast, flowing into the milk receiving bag 19 through the milk extracting conduit 42.

When the lever body 50 of the pressure release lever 45 is pressed, the projection 51 presses the valve 58 against the force of the spring 47. A clearance is created between the tapered portion of the valve 48 and the hole 49a of the valve receiving member 49, which connects the atmosphere with the inside of the extracting cup 41 through the release path 46. The suction or negative air pressure in the extracting cup 41 is thus released. The extracting cup 41 can then easily be disengaged from the breast.

The suction pressure in the container 52 and the extracting cup 41 can easily be adjusted by the rotation of the knob 81 of the pressure adjusting mechanism 61. When the knob 81 is rotated, the rotating plate 85 rotates together with the knob. The fan shaped cut out 94 of the rotating plate 85 is rotated to a particular air path hole 89, and air can pass through the air path hole 89 of the air path plate 84.

The air path holes 89 in the air path plate 84 connect with the air path 70 through the nozzle holes 88 of the nozzle plate 83. Each nozzle hole 88 has a different diameter, and air according to the diameter of the particular nozzle hole 88 chosen can flow into the air path 70 from the atmosphere. The amount of air that flows into the air path 70 is thus adjusted by choosing a particular nozzle hole 88, and thus adjusting the negative air pressure applied.

When the knob 81 is rotated, the projection 93 that is formed on the end of the arc-shaped arm 92 on the rotation plate 85 moves between the V-shaped notches in the opening 76 of the body 75 against the outward elastic force of the arm 92. Accordingly, the rotating plate 85 can be positioned step-by-step in the V-shaped notches 80.

Note that in the present embodiment, the nozzle portion includes the nozzle plate 83 and the air path plate 84. However, note that the nozzle portion can be constructed with the nozzle plate 83 only. Also note that the member 25 of the milk receiving bag 19 can be constructed with the cylindrical portions 26 and the flange 27 only, without the sealing plate 28.

A further embodiment of the cap of the milk receiving bag 19 will now be described with reference to FIGS. 15-20. Having a refrigerator with a freezer in the home has popularized the practice of preserving extracted milk by freezing. When reused, the frozen milk is warmed to a suitable temperature, about 40° C., and then fed to a baby. Usually, a nursing bottle or other sealable bottles are used as containers for freezing and preserving the milk.

Figure 19:
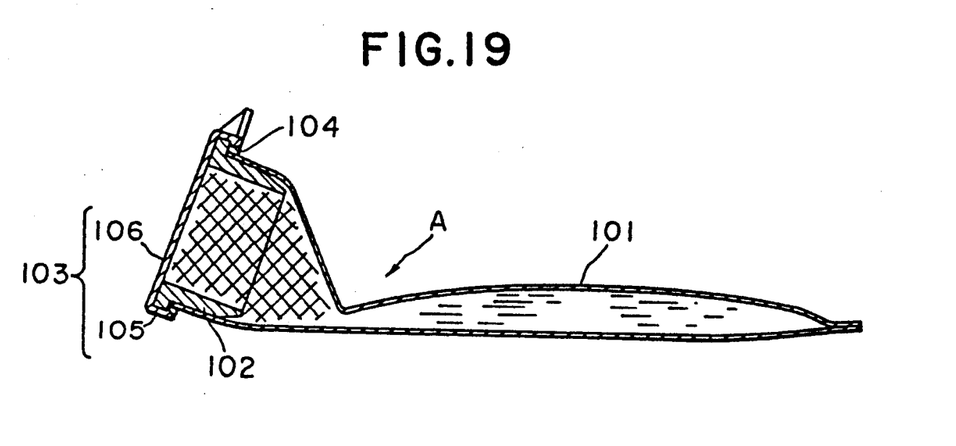
FIG. 19 is a sectional view of a conventional milk receiving bag.

A container as shown in FIG. 19 has been known to be most suitable for freezing and preserving milk. This container comprises a bag 101, a mouth 102 fixed to an opening of the bag 101 and a cap 103 fixed to the mouth 102 for sealing the opening of the mouth. Each of these members is made of vinyl. The cap 103 includes a cylindrical portion 105 which has a circular projection 104 formed thereon for gripping a peripheral edge of the mouth 102, thus preventing the cap 103 from coming off of the mouth 102. A cap surface 106 seals the opening of the mouth 102.

Figure 20:
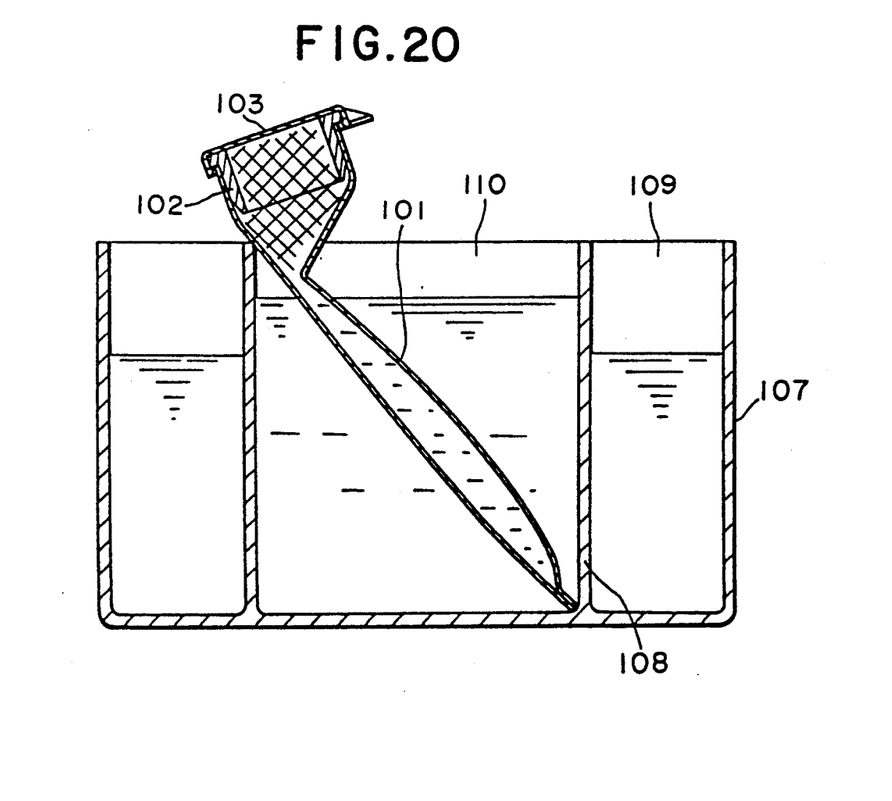
FIG. 20 is a sectional view showing the defrosting of frozen milk in a conventional milk receiving bag.

When milk frozen in a bag, such as bag 101 of FIG. 19, is to be used, the frozen milk is defrosted in a container, such as container 107 as illustrated in FIG. 20. This container 107 has an inner tank 110 and an outer tank 109 divided by a cylindrical partition plate 108. Water is contained in the inner tank 110, and hot water, above 90° C., is contained in the outer tank 109. The bag 101 is immersed in the inner tank 110, and the frozen milk is slowly defrosted by the water in the inner tank 110, which is warmed by the hot water in the outer tank 109. The defrosted milk is thus warmed to a temperature suitable for feeding a baby, about 40° C. Since the container 107 has two separate tanks, the frozen milk may be defrosted slowly. Accordingly, the ingredients of the milk are not damaged.

It is desirable that air in the milk receiving bag, or milk preserving bag in this case, is removed to as great an extent as possible for the best conditions of preservation. But since the milk preserving bag 101 having the cap 103 is laid on its side in the freezer, a large cylindrical lump of ice is produced at the inside of the mouth 102, as illustrated by the crossed oblique lines in FIGS. 19 and 20. Such a large lump of ice cannot easily be melted by the warm water of relatively low temperature in the inner tank 110. This results in a long period of time being taken to warm the milk to a suitable temperature for feeding a baby.

Accordingly, the present invention provides a milk preserving bag wherein the lump of ice that is formed at the mouth 102 is reduced in size to as great an extent as possible.

Noting FIGS. 15-18, bag 111 has a mouth 112 and a cap 113. Each of these members is made of vinyl. The bag 111, further, is formed by heat sealing. The mouth 112 is inserted into the opening of the bag 111, and the mouth 112 is fixed to the opening by heat sealing.

Figure 15:
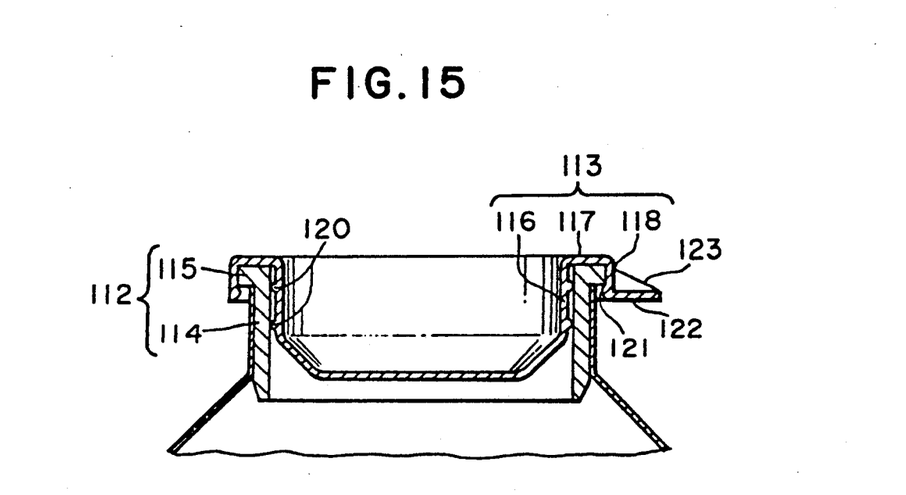
FIG. 15 is a cross-sectional view of a cap portion of a milk receiving bag.
Figure 16:
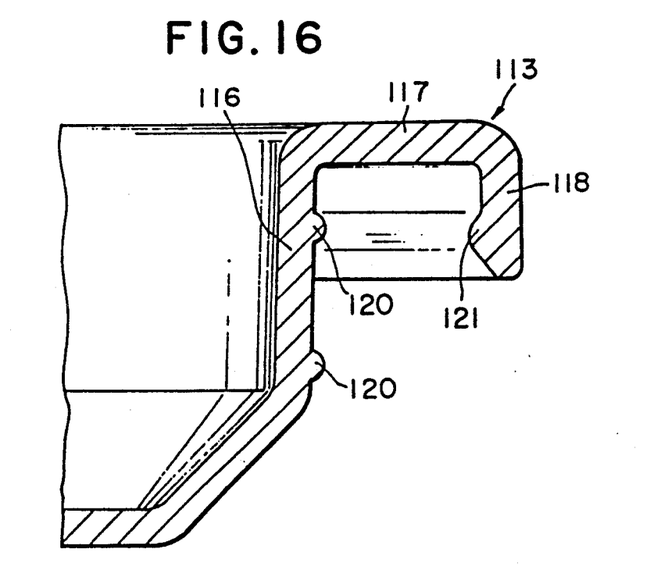
FIG. 16 is an enlarged sectional view of a main part of the cap of FIG. 15.

The mouth 112 is cylindrical and has a cylindrical portion 114 fitting into the opening of the bag 111, as well as a flange 115. The cap 113 covers the mouth 112, and includes an inner cylindrical portion 116, an edge portion 117 and an outer cylindrical portion 118.

Preferably, at least one circular projection 120 is formed on the outer side of the inner cylindrical portion 116 for providing a seal between the cylindrical portion 114 of the mouth 112 and the inner cylindrical portion 116 of the cap 113. A circular projection 121 is provided on the inner side of the outer cylindrical portion 118 for preventing the cap from coming off of the flange 115 of the mouth 112.

A lug 122 is provided on the outer cylindrical portion 118 for pulling off the cap 113. A rib 123 reinforces the lug 122.

Figure 17:
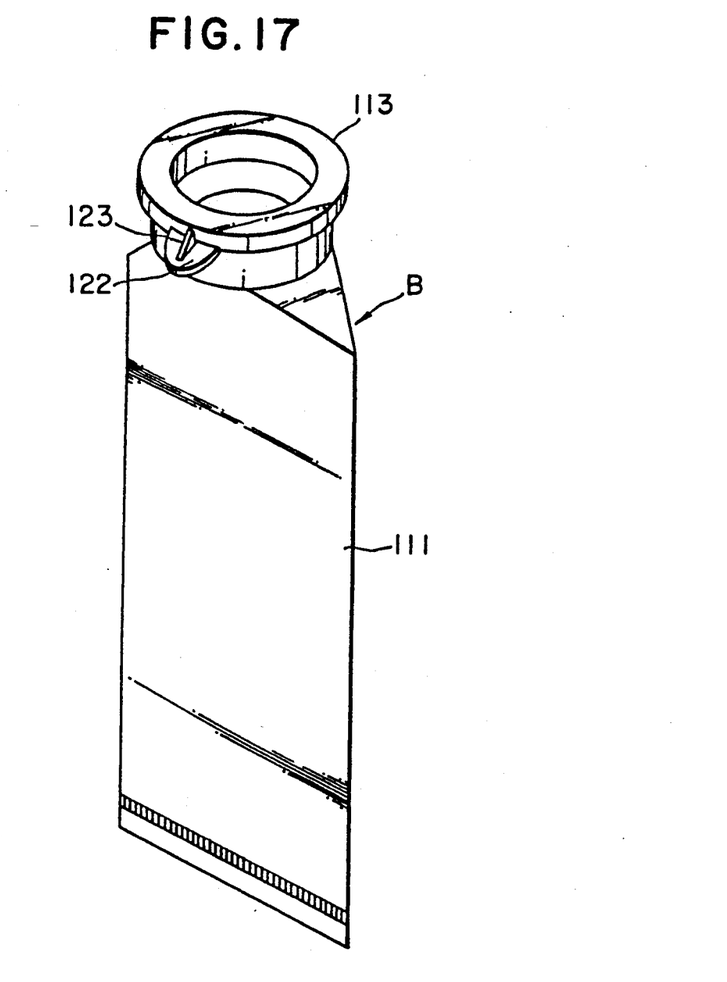
FIG. 17 is a perspective view illustrating the mounting of the cap to a milk receiving bag body.
Figure 18:
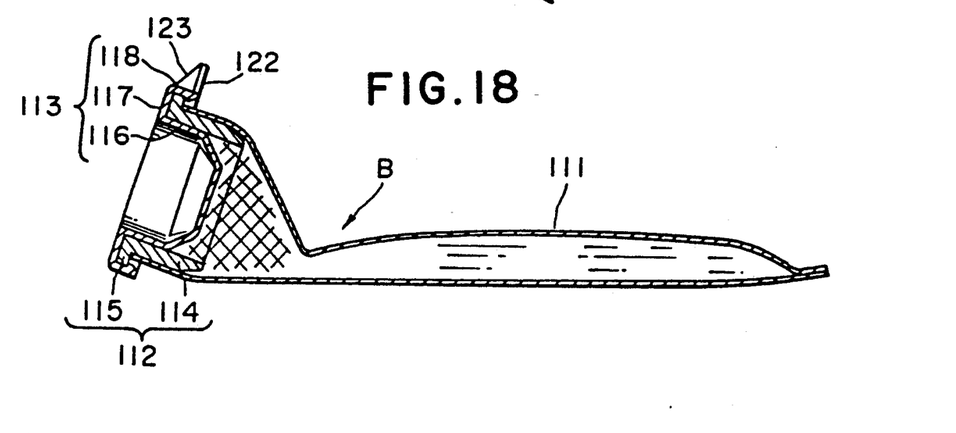
FIG. 18 is a sectional view of the milk receiving bag body of FIG. 17.

The milk preserving bag according to the above-described embodiment is used as follows. The bag 111, which contains the milk extracted by the breast pump, is rubbed from bottom to top with the hand of the user to remove the remaining air inside the bag 111. The level of the milk in the bag is thus lifted to the bottom of the inner cylindrical portion 114, and then the cap 113 is fitted into the mouth 112.

The circular projection 120 of the inner cylindrical portion 116 is then pressed against the inner wall of the cylindrical portion 114 of the mouth 112. A seal is thus formed between the cylindrical portion 114 and the inner cylindrical portion 116. The cap 113 is fixed to the mouth 112 by the circular projection 121 of the outer cylindrical portion 118.

The cap 113, with the inner cylindrical portion 116, thus provides an intrusive portion intruding into the mouth 112 and displacing the space normally available for milk inside the mouth 112. Accordingly, when the bag with the air removed as described above is frozen inside the freezer, only a small quantity of ice is produced near the mouth 112. Note the crossed diagonal lines illustrated in FIG. 18. This is because the inner cylindrical portion 116 extends to the bottom of the cap 113 and has a bottom surface extending there across, thus displacing the space normally available inside the inner cylindrical portion 114 of the mouth 112.

The frozen milk is subsequently defrosted by the container 107 as illustrated in FIG. 20. The milk receiving bag 101 is immersed in the inner tank 110 containing water. The milk receiving bag B is slowly warmed together with the water in the inner tank 110 by the hot water, approximately 90° C., in the outer tank 109. The defrosted milk is warmed until it is about 40° C. and then fed to the baby.

The present invention as has been discussed above has the following distinct advantages. First, the milk may be extracted into the milk receiving bag directly, and thus the milk extracted can be preserved in the freezer without moving the milk into another container. This ensures sanitary conditions and involves less trouble than with the prior arrangements. Second, since the extracted milk does not touch the container or the negative air pressure source, it is unnecessary to wash the negative pressure source or the container. Third, if any pain or discomfort is experienced while the milk is being extracted, due to the negative air pressure, the breast pump can easily be removed by simply operating the pressure releasing mechanism. Lastly, because frozen milk in the milk receiving bag can be defrosted slowly, since no inordinately large lumps of ice are present at the mouth of the bag, damage to the ingredients of the milk is prevented.

Although the present invention has been described and illustrated with respect to various embodiments and preferred features thereof, it is to be understood that modifications may be made to the specifically described and illustrated embodiments without departing from the scope and spirit of the present invention.

What is claimed:

1. A breast pump, comprising:

an extracting cup having one end having an engagement portion for engagement with a breast and an opposite end;

a container having a mouth portion connected to said extracting cup at said opposite end, said container having an interior space;

a milk receiving bag for mounting to said mouth portion of said container and suspension in said interior space of said container;

an air suction source connected to said container for producing an air suction condition in said interior space of said container;

a first air path defined between and fluidly connecting the interior of said extracting cup and said interior space of said container; and a pressure adjusting means for adjusting the suction pressure on a breast in said extracting cup, comprising:

a body portion defining a second air path communicating with said interior space of said container and first air path and an opening communicating with said second air path, a nozzle portion having a plurality of different diameter nozzle holes therein communicating with said second air path, said nozzle portion being fixed in said opening, a rotating member rotatably mounted in said opening having a portion therein for selectively allowing a single said nozzle hole to communicate said second air path with the exterior of said container, and a knob rotatably mounted on said body portion and connected to said rotating member for rotation thereof.

2. The breast pump of claim 1, and further comprising:

a suction release means fluidly connecting the interior of said extracting cup with the outside environment for releasing the suction on a breast in said extracting cup.

3. The breast pump of claim 2, wherein said suction release mechanism comprises:

a release opening formed in said extracting cup;

a valve seat provided in said release opening, said valve seat having an opening therein;

a valve movably mounted for engagement with said opening of said valve seat in said release opening;

a spring biasing said valve in said release opening toward a position closing said opening of said valve seat; and a suction release lever movably mounted in said opening of said valve seat for moving said valve off of said valve seat.

4. The breast pump of claim 1, wherein:

said air suction source has a suction conduit connected to said container; and said pressure adjusting means is connected to said suction conduit.

5. The breast pump of claim 4, wherein said air suction source further comprises a motorized air pump fluidly connected to said suction conduit.

6. The breast pump of claim 1, wherein said nozzle portion comprises a nozzle plate having said plurality of nozzle holes therein and an air path plate on said nozzle plate having a plurality of protrusions defining air path holes corresponding to said nozzle holes of said nozzle plate.

7. The breast pump of claim 6, wherein said body portion has a protrusion extending through said nozzle plate and into a said air path hole of said air path plate.

8. The breast pump of claim 6, wherein said second air path comprises a partially annular groove in said body portion in communication with each of said nozzle holes and air path holes.

9. The breast pump of claim 6, wherein said rotating member comprises a disc covering said air path holes and said portion of said rotating member is a cut-out in said disc.

10. The breast pump of claim 1, wherein said body portion has a plurality of notches therein and said rotating member has a resiliently mounted projection thereon for engagement with said notches upon rotation thereof.

11. The breast pump of claim 1, wherein said air suction source comprises a pump fluidly connected to said interior space of said container.

12. The breast pump of claim 11, wherein said pump is a manual pump connected to a bottom cap of said container.

13. The breast pump of claim 11, wherein said pump is a motorized pump mounted on a portion of said container.

14. The breast pump of claim 13, wherein said motorized pump has an electric motor, a diaphragm pump connected to said electric motor and a power supply for said electric motor.

15. The breast pump of claim 14, wherein said container has a bottom cap with an air passage therethrough and a holder mounted to said bottom cap, said holder holding said diaphragm pump, said electric motor and said power supply on said bottom cap.

16. The breast pump of claim 1, wherein said milk receiving bag comprises a bag body having a sealed end and an open end, a mouth piece mounted in said open end sealed thereto, said mouth piece comprising a cylindrical portion and a seal plate sealing said mouth piece and said bag body, and a lid.

17. The breast pump of claim 16, wherein said seal plate has a annular groove and a pull ring for unsealing said bag body.

18. An adjustable pumping mechanism for use with a container, comprising:

a diaphragm pump for producing air suction inside a container, said pump having a suction inlet for communication with the container;

a body portion having an air path communicating with said suction inlet and communicatable with the container, and an opening communicating with said air path;

a nozzle portion having a plurality of different diameter nozzle holes therein communicating with said air path, said nozzle portion being fixed in said opening;

a rotating member rotatably mounted in said opening having a portion therein for selectively allowing a single said nozzle holes to communicate said air path with the exterior of said opening; and a knob rotatably mounted on said body portion and connecting to said rotating member for rotation thereof.

19. The adjustable pumping mechanism of claim 18, wherein said nozzle portion comprises a nozzle plate having said plurality of nozzle holes therein and an air path plate on said nozzle plate having a plurality of protrusions defining air path holes corresponding to said nozzle holes of said nozzle plate.

20. The adjustable pumping mechanism of claim 19, wherein said body portion has a protrusion extending through said nozzle plate and into a said air path hole of said air path plate.

21. The adjustable pumping mechanism of claim 19, wherein said air path comprises a partially annular groove in said body portion in communication with each of said nozzle holes and air path holes.

22. The adjustable pumping mechanism of claim 19, wherein said rotating member comprises a disc covering said air path holes and said portion of said rotating member is a cut-out in said disc.

23. The adjustable pumping mechanism of claim 18, wherein said body portion has a plurality of notches therein and said rotating member has a resiliently mounted projection thereon for engagement with said notches upon rotation thereof.

24. A breast pump, comprising:
 an extracting cup having one end having an engagement portion for engagement with a breast and an opposite end;
 a container having a mouth portion connected to said extracting cup at said opposite end, said container having an interior space;
 a milk receiving bag for mounting to said mouth portion of said container and suspension in said interior space of said container;
 an air suction source connected to said container for producing an air suction condition in said interior space of said container; and
 a first air path defined between and fluidly connecting the interior of said extracting cup and said interior space of said container;
 wherein said extracting cup has a milk extracting conduit communicating with said engagement portion and a connecting portion at said opposite end of said conduit for connecting said extracting cup to said mouth of said container;
 wherein said container has an upper end defining said mouth portion with external threads thereon, said milk receiving bag has a flange to be supported on top of said upper end and said connecting portion of said extracting cup has internal threads engaging said external threads of said upper end of said container and holds said flange of said bag on said upper end; and
 wherein said first air path extends between said upper end of said container and said bag and said flange of said bag, and between said flange and said connecting portion of said extracting cup, said first air path comprising grooves in said flange.

* * * * *